United States Patent

Huchon et al.

[11] Patent Number: 5,259,378
[45] Date of Patent: Nov. 9, 1993

[54] PHONATION DEVICE FOR TRACHEOTOMY PATIENTS INCLUDING A CHECK VALVE AND FILTERING MEANS

[76] Inventors: Jean-Michel Huchon, Chaux La Lotiere, Rioz, France, 70190; Philippe Vannson, Chemin du Salon, Laverney, Recologne, France, 25170

[21] Appl. No.: 671,711

[22] PCT Filed: Jun. 1, 1990

[86] PCT No.: PCT/FR90/00382
§ 371 Date: Apr. 5, 1991
§ 102(e) Date: Apr. 5, 1991

[87] PCT Pub. No.: WO90/14854
PCT Pub. Date: Dec. 13, 1990

[30] Foreign Application Priority Data
Jun. 5, 1989 [FR] France ................... 89 07625

[51] Int. Cl.5 .............. A62B 18/08; A62B 9/02; A62B 9/06; A61M 16/00
[52] U.S. Cl. .................. 128/207.16; 128/201.13
[58] Field of Search ............ 128/207.14, 207.15, 128/207.16, 204.17, 911, 912, 207.29, 200.24, 200.26, 201.13; 623/9

[56] References Cited

U.S. PATENT DOCUMENTS

| 3,683,931 | 8/1972 | Chelucci et al. | 128/207.14 |
| 4,040,428 | 8/1977 | Clifford | 128/207.16 |
| 4,202,330 | 5/1980 | Jariabka | 128/207.14 |
| 4,325,366 | 4/1982 | Tabor | 128/207.16 |
| 4,538,607 | 9/1985 | Saul | 128/207.16 |
| 4,582,058 | 4/1986 | Depel et al. | 128/207.16 |
| 4,759,356 | 7/1988 | Muir | 128/207.16 |
| 4,971,054 | 11/1990 | Andersson et al. | 128/207.14 |
| 5,042,468 | 8/1991 | Lambert | 128/200.24 |

FOREIGN PATENT DOCUMENTS

| 8701414 | 5/1987 | Fed. Rep. of Germany . |
| 2559067 | 8/1985 | France . |
| 201960 | 2/1966 | Sweden ............ 128/207.14 |

Primary Examiner—Edgar S. Burr
Assistant Examiner—Kimberly L. Asher
Attorney, Agent, or Firm—Bacon & Thomas

[57] ABSTRACT

A phonation and respiratory aid device for a tracheotomy patient comprising a tracheotomy cannula, a non-return valve for permitting inhalation flow only, the valve being distorted both axially and radially due to inhalation, a connecting means for connection to a source of fluid from a forced oxygenation device, the connecting means being upstream of the valve in the inhalation flow direction, and two filtering elements also upstream of the valve, the filtering elements including a Venturi tube.

11 Claims, 2 Drawing Sheets

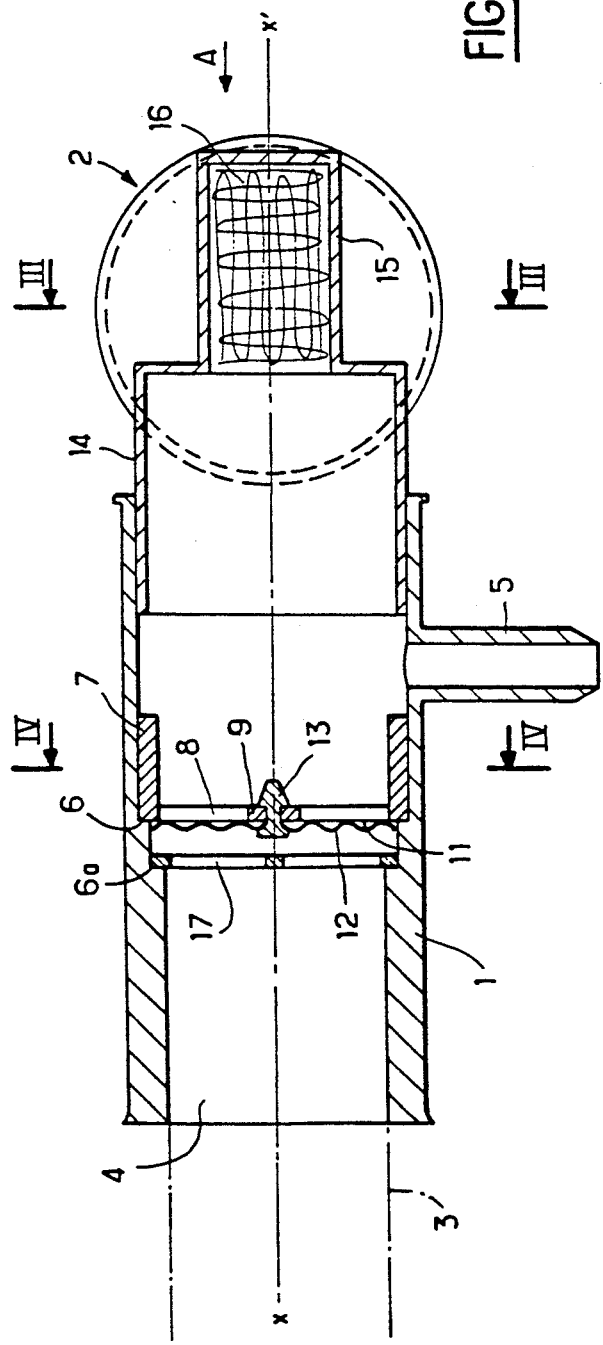
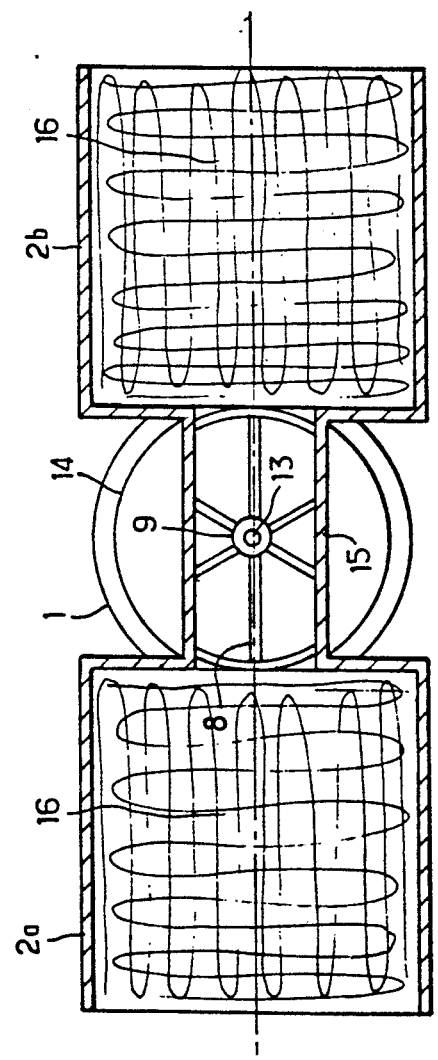
FIG. 2
FIG. 3

PHONATION DEVICE FOR TRACHEOTOMY PATIENTS INCLUDING A CHECK VALVE AND FILTERING MEANS

TECHNICAL FIELD

The present invention relates to valves and respiratory aid devices which are placed in position on patients having undergone a tracheotomy.

This operation, which consists in opening the trachea in order to re-establish respiration, is indicated in the case of serious disease of the larynx, such as an oedema of the glottis or, for example, a serious chronic respiratory insufficiency by obstructive, restrictive or severe mixed syndrome.

After the trachea has been opened, a cannula, called tracheotomy cannula, is placed in position, through which the outside air can penetrate, thus ensuring pulmonary ventilation and aspiration of the bronchial mucosities.

The implantation of a tracheotomy cannula in the trachea of a patient generally does not allow the passage of the inhaled air in the direction of the upper respiratory tracts whose task is to ensure functioning of the vocal chords to allow the patient fitted with the apparatus to express phonemes.

PRIOR ART

To allow patients, in whose trachea a tracheotomy cannula is implanted, to conserve the possibility of expressing phonemes, it has already been proposed to dispose, at the outer end of the channel of the tracheotomy cannula, a valve including a non-return flap valve allowing the inhaled flow of air to penetrate in the trachea, whilst the exhaled air is blocked by the non-return valve inside the trachea and is thus conducted and forced towards the patient's vocal chords, insofar as the type of tracheotomy cannula allows this. Such prior devices are for example illustrated in application DE-U-8,701,414 which proposes mounting, inside an adapting piece added to the end of the tracheotomy cannula, a curved rigid flap valve elastically pre-stressed in abutment against an annular seat. Such an embodiment is delicate to produce, due in particular to the difficulty to adjust and maintain the curve and pre-stress of the flap valve at values allowing both normal respiration and phonation. Furthermore, such an embodiment does not allow connection to a forced oxygenation installation without removing the adapting piece comprising the flap valve.

In certain cases, it so happens that the haematosis function of tracheotomized patients spontaneously proves to be insufficient, this requiring the connection on the cannula of a source of additional oxygen ensuring forced oxygenation.

In such situations, the devices of the prior art have proved unsuitable for ensuring both the function of phonation and the function of forced oxygenation leading, in the case of connection of the oxygenation installation, to removing the non-return valve and replacing it by an adapter. The patient, who is then in a state of forced oxygenation, can no longer speak, which obviously presents a certain disadvantage for the patient and in particular involves particularly negative psychological consequences.

U.S. Pat. No. 3,683,931 is also known, which describes a rigid valve axially mobile inside the channel of an adapter and maintained in elastic abutment via a helical spring. Such an embodiment is also delicate to produce and the adjustment of the elasticity of the spring, which determines the reliability of the device, proves difficult. It is provided to connect the device to a source of fluid, of the nebulizer type, without forced oxygenation.

The object of the invention aims at producing a phonation and respiratory aid device for a patient having undergone a tracheotomy, not presenting the drawbacks of the prior art devices and enabling the patient to conserve the use of speech, whilst having the possibility of undergoing a forced oxygenation.

Another object of the invention aims at producing an oxygeno-phonation valve including a non-return flap valve whose functioning is particularly reliable and which may be replaced simply.

Another object of the invention is to propose a respiratory aid device comprising a tracheotomy cannula and an oxygeno-phonation valve ensuring, in complete safety and for a long-lasting period, the functions of oxygenation and phonation.

SUMMARY OF THE INVENTION

The objects of the present invention are attained thanks to a phonation and respiratory aid device for a tracheotomized patient, comprising a tracheotomy cannula tip defining a channel, a non-return valve for preventing passage of the exhaled air flow and for allowing passage of the inhaled air flow, a support means for said flap valve disposed downstream of a means for connection to a source of fluid with respect to the inhaled air flow, characterized in that:

the support means is interposed in the channel and comprises a support face forming a transverse wall allowing air to flow through, the flap valve is mounted, by a fixing means defining a fixing area, against said transverse wall and downstream of the latter with respect to the inhaled air flow, said flap valve being constituted by a flexible material that can be distorted so as to allow, on the one hand, its distorsion both axially and radially from its fixing area under the effect of the inhaled air flow and, on the other hand, it to be maintained in sealed relationship against the transverse wall under the effect of the exhaled air flow, the connecting means is a connection grip provided in the tip and adapted for connection to a forced oxygenation appliance.

Various other characteristics will appear from the following description with reference to the accompanying drawings, which show, by way of non-limiting examples, embodiments of the object of the invention.

BRIEF DESCRIPTION OF THE DRAWINGS

FIG. 2 is a view of the device according to the invention, taken along a longitudinal section.

FIG. 3 is a view in section of the device according to the invention, taken along line III—III of FIG. 2.

FIG. 1 shows a general view of a respiratory aid device adapted to be implanted in the trachea of a patient and comprising a tip 1 on which is mounted a unit 2 for filtration of the air flow.

BEST MANNER OF IMPLEMENTING THE INVENTION

Figure 4:
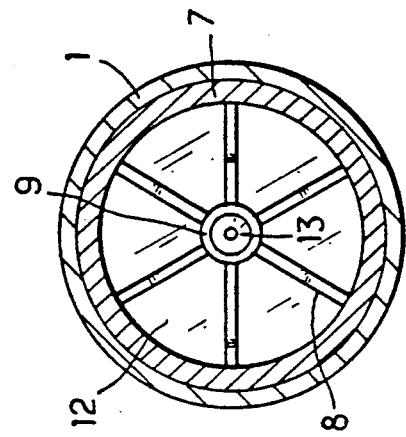
FIG. 4 is a view taken along a transverse section made along line IV—IV of FIG. 2.

The examples represented in FIGS. 1 to 4, show tips 1 of tracheotomy cannulae, as well as filtration units 2, which present cylindrical cross sections. It is obvious that the cross sections of these two elements may present other geometrical shapes and the cross sections may in particular present square, diamond, hexagonal or rectangular shapes without departing from the scope of the invention.

The tip 1, represented in FIG. 2, is generally implanted on the patient via a tracheotomy cannula 3 shown schematically in FIG. 2. The tip 1 of the tracheotomy cannula 3, which may be made of plastics material for example, defines an inner channel 4 whose diameter is preferably substantially constant along the tip 1.

A grip 5 for connection to an annexed oxygenation device, is provided in the tip 1 and comprises a tubular connection proper and a bore through the wall of the tip 1. The tubular connection is preferably radial and perpendicular to the principal axis of the channel 4.

The channel 4 preferably comprises at least one annular shoulder 6 formed downstream of the connection grip 5 with respect to the inhaled flow of air, of which the direction is represented by arrow A. These inner shoulders 6 are used as members for positioning elements intended to be positioned in the channel 4.

The respiratory aid device according to the invention comprises a phonation valve constituted by a support means 7 disposed in channel 4. The support means 7 is preferably a bush added and blocked in position in the channel 4 of the cannula against the annular shoulder 6. The bush comprises a transverse wall extending through the section of the channel 4. The wall thus defined is permeable to the inhaled and exhaled air flow and is preferably constituted by a series of cross pieces 8 constituting orifices for passage of the air flow. The cross pieces 8 join in a substantially central zone constituted by a ring 9.

The thickness of the transverse wall of the support means 7, in the present case the bush, defines a downstream face 11 with respect to the inhaled air flow A, forming a support face for a non-return flap valve 12 mounted in sealed relationship against face 11. The shape of the non-return valve 12 is chosen such that it completely obstructs the channel 4 and is maintained in sealed abutment, preferably by a clip 13 engaged by force in the central part of the ring 9 and elastically blocked in the ring 9.

The non-return flap valve 12 is chosen to be made of a flexible, elastic material, such as latex, siliconed or not, capable of presenting properties of distorsion from the fixing area defined by the fixed connection between the non-return valve 12 and the support means 7, namely the clip 13 and the ring 9. These properties of distorsion include a radial distorsion from the fixing area and axial, i.e. in the direction of the inhaled air flow.

It must be considered that the support face of the bush advantageously comprises at least two crosspieces 8, but that other equivalent means may also be employed such as, for example a grating assembly constituted by bars or an assembly provided with orifices of circular shape, for example. It can also be envisaged to produce the support and fixing area of the non-return valve on the bush in an eccentric area with respect to axis x—x' of the tip 1, even in an area located on the outer circumference of the bush. Of course, it can also be envisaged, more particularly in the last case mentioned, to provide a plurality of points of fixing of the non-return valve 12 on the bush 7.

FIG. 2 also shows that the non-return valve 12 is preferably constituted by a series of undulations adapted to give it accentuated flexibility and elasticity.

Figure 1:
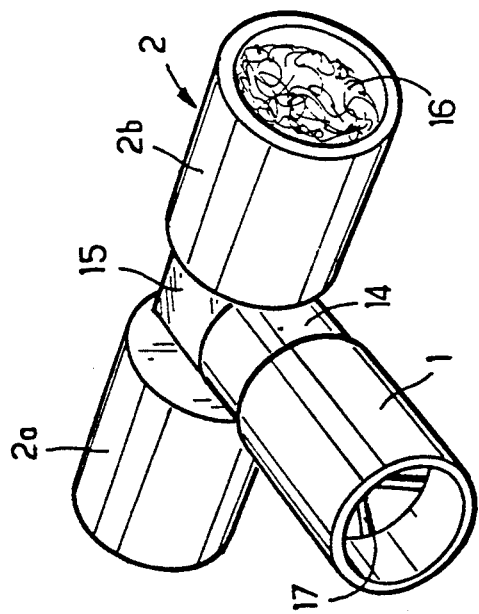
FIG. 1 is a view in perspective of the device according to the invention.

The end opposite that part of the tip 1 which is positioned on the tracheotomy cannula 3, is intended to receive a filtration unit 2 which, in the embodiments shown in FIGS. 1 and 3, is preferably constituted by two filtering elements 2a and 2b.

The filtration unit 2 comprises an adapting tip 14, of section virtually identical to that of tip 1, in order to be able to be inserted by force and in sealed manner inside the channel 4 and to be blocked in position therein by means, for example, of systems of the jaw type. The adapting tip 14 extends by two diverging branches 2a and 2b which may be of cylindrical section, with longitudinal axes perpendicular to the axis x'x' of the tip 1, so as to give the filtration unit 2 the general form of a "T". The join between the two diverging branches 2a, 2b and the tip 14, is constituted by a transition zone 15 of which the cross section is of dimensions smaller than the cross section of each of the diverging branches 2a, 2b, to constitute a Venturi tube. The filtration elements are advantageously composed of filtering cartridges 16 introduced in each of the branches 2a, 2b and coming into abutment against the shoulders of each of the branches 2a, 2b resulting from the reduction in section of the zone of join 15. It can also be envisaged to provide a system for regulation of the Venturi effect with manual control.

It is obvious that, in place of a filtration unit 2 provided with two diverging branches forming a "T", a filtration unit comprising one single branch located in line with tip 1, may also be envisaged. It is also possible to produce a filtration unit comprising more than two filtration cartridges 16.

During inhalation of the air flow effected by the patient, the inhaled air is firstly filtered inside the cartridges 16, then is accelerated by the Venturi system formed by the reduction in section of the zone of join 15, to exert a pressure on the non-return valve 12 which then distorts radially and axially in the direction of the inhaled air flow A in order to allow the air flow to penetrate in the patient's larynx.

Upon exhalation of the air flow, the non-return valve 12 is applied in sealed manner against the support face of the bush and thus forms an obstacle to the passage of the air through the cannula 4, then enabling the patient to use the air imprisoned in the trachea to vibrate his/her vocal chords. If the state of the patient requires a forced oxygenation, the oxygen penetrates through the connection grip 5 and radially deforms the non-return valve 12, in the same manner as defined previously, and is then blocked inside the patient's larynx, enabling him to conserve the use of speech, even in a situation of forced oxygenation, the connection grip 5 lying upstream of the non-return valve 12 with respect to the inhaled air.

It may also be envisaged to provide a second annular shoulder 6a located downstream of the annular shoulder 6 adapted to receive the support means 7, in order to serve as seat for receiving a safety device constituted by a separation wall 17 of the channel 4 capable of preventing passage of the non-return valve 12 in the patient's trachea. In fact, by reason of a failure of the fixing means 13, it may happen that the non-return valve 12 be led, during inhalation, to penetrate in the trachea. To that end, the separation wall 17 advantageously consists in a disc rendered permeable to the air flow, by means of orifices provided in its thickness. Permeability of the wall 17 may be obtained by a crosspiece structure, similar to that described for the support face of the support means 7, or may consist in a grating or perforated structure.

The device thus described enables a tracheotomized patient to conserve the use of his/her vocal chords, even in the case of forced oxygenation, thanks to the valve and to the oxygeno-phonation device proposed. Assembly of the non-return valve 12 on a support means 7 added inside the channel 4 allows, if necessary, an easy and rapid change of the phonation valve.

The invention is not limited to the examples described and shown, as various modifications may be made thereto without departing from its scope and, in particular, a plurality of non-return valves may be disposed in the section of channel 4.

POSSIBILITY OF INDUSTRIAL APPLICATION

The invention finds a preferred application in the production of tips of tracheotomy cannulae connected to forced oxygenation appliances in order to constitute oxygeno-phonation devices.

We claim:

1. A phonation and respiratory aid device for a tracheotomized patient, comprising a tracheotomy cannula having a tip, means defining a channel in said tip, means including a non-return flap valve for preventing passage of an exhaled air flow and for allowing passage of an inhaled air flow, connecting means for permitting connection of said cannula to a source of fluid, support means for supporting said flap valve, said support means disposed downstream of said connecting means with respect to the inhaled air flow, wherein:

said support means is interposed in said channel and comprises means including a support face forming a transverse wall for allowing air to flow through;

fixing means defining a fixing area for mounting said flap valve against said transverse wall and downstream of said support means with respect to the inhaled air flow, said flap valve comprising a flexible material arranged to distort both axially and radially away from said fixing area as a result of the inhaled air flow and to be maintained in sealed relationship against said transverse wall as a result of the exhaled air flow, and wherein said connecting means is a connection grip provided in said tip and said source of fluid to which the connection means is connected is a forced oxygenation appliance.

2. A device as claimed in claim 1, wherein said support means comprises a bushing fixed in said channel.

3. A device as claimed in claim 2, wherein said support face comprises two support face crosspieces joined at a common zone, said common zone forming said fixing area.

4. A device as claimed in claim 3, wherein said fixing means is a fixing clip tightened between said flap valve and said common zone of said crosspieces, thereby defining said fixing area at a location substantially central to said channel and to a surface of said flap valve.

5. A device as claimed in claim 1, further comprising a separation wall which is permeable to air flow, and is interposed and fixed in said channel downstream of said flap valve with respect to the inhaled air flow.

6. A device as claimed in claim 5, wherein said separation wall comprises separation wall crosspieces.

7. A device as claimed in claim 1, further comprising means including a filtering unit for filtering the inhaled air flow, the filtering unit being disposed upstream of said grip with respect to the inhaled air flow.

8. A device as claimed in claim 7, wherein said filtering unit comprises means including an adapting tip for insertion into said channel, and at least one filtration cartridge.

9. A device as claimed in claim 8, wherein said adapting tip comprises a transition zone forming a Venturi tube.

10. A device as claimed in claim 8, wherein said adapting tip is extended by two diverging branches, each branch comprising a filtration cartridge.

11. A device as claimed in claim 10, wherein a joint between said two diverging branches and said adapting tip comprises a transition zone having a cross section which is smaller than cross sections of said diverging branches to form a Venturi tube.

* * * * *